United States Patent
Feller, III et al.

(10) Patent No.: US 7,811,300 B2
(45) Date of Patent: Oct. 12, 2010

(54) THIN FILM DEVICES FOR TEMPORARY OR PERMANENT OCCLUSION OF A VESSEL

(75) Inventors: Frederick Feller, III, Maple Grove, MN (US); Donald K. Jones, Dripping Springs, TX (US); Darren R. Sherman, Fort Lauderdale, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 826 days.

(21) Appl. No.: 11/662,816

(22) PCT Filed: Sep. 16, 2005

(86) PCT No.: PCT/US2005/033388
§ 371 (c)(1), (2), (4) Date: Mar. 14, 2007

(87) PCT Pub. No.: WO2006/034140
PCT Pub. Date: Mar. 30, 2006

(65) Prior Publication Data
US 2008/0195136 A1 Aug. 14, 2008

Related U.S. Application Data

(60) Provisional application No. 60/610,777, filed on Sep. 17, 2004.

(51) Int. Cl.
*A61B 17/08* (2006.01)
(52) U.S. Cl. ..................................................... 606/157
(58) Field of Classification Search ................ 606/108, 606/151, 157, 159, 200, 191–198; 623/1.11–1.12
See application file for complete search history.

(56) References Cited

U.S. PATENT DOCUMENTS

| 5,382,261 A | 1/1995 | Palmaz |
| 5,474,563 A | 12/1995 | Myler et al. |
| 6,221,086 B1 * | 4/2001 | Forber .......................... 606/151 |
| 6,312,407 B1 | 11/2001 | Szadno-Azizi et al. |

(Continued)

FOREIGN PATENT DOCUMENTS

DE  199205797 U1  7/1992

(Continued)

OTHER PUBLICATIONS

European Search Report EP 05799706 dated Oct. 29, 2009.

*Primary Examiner*—Kevin T Truong

(57) ABSTRACT

Thin film devices implantable within a human subject for occlusion of an aneurysm or body vessel are provided. The devices are movable from an elongated, collapsed configuration for delivery to a deployed configuration within the body. Open slots in selected portions of the device telescope as the device moves to its deployed configuration, which causes the associated portions to longitudinally foreshorten and radially expand, while also decreasing in porosity for preventing blood flow. Closed slits in other portions of the device open as the device moves to its deployed configuration, which causes the associated portions to longitudinally foreshorten and radially expand, while remaining open for fluid flow or endothelialization. The occlusion devices may be either self-supporting or supported by a strut structure. Additionally, the occlusion devices may comprise a plurality of mesh layers having unaligned pore systems which further reduce porosity in desired portions of the deployed configuration.

21 Claims, 3 Drawing Sheets

U.S. PATENT DOCUMENTS

| | | |
|---|---|---|
| 6,632,236 B2 | 10/2003 | Hogendijk |
| 6,635,068 B1 | 10/2003 | Dubrul et al. |
| 6,695,865 B2 | 2/2004 | Boyle |
| 6,726,701 B2 * | 4/2004 | Gilson et al. ................. 606/200 |
| 6,936,055 B1 * | 8/2005 | Ken et al. ................... 606/157 |
| 2001/0041858 A1 | 11/2001 | Ray et al. |
| 2004/0098094 A1 * | 5/2004 | Boyle et al. ................ 623/1.13 |

FOREIGN PATENT DOCUMENTS

WO     WO 9912484 A1     3/1999

* cited by examiner

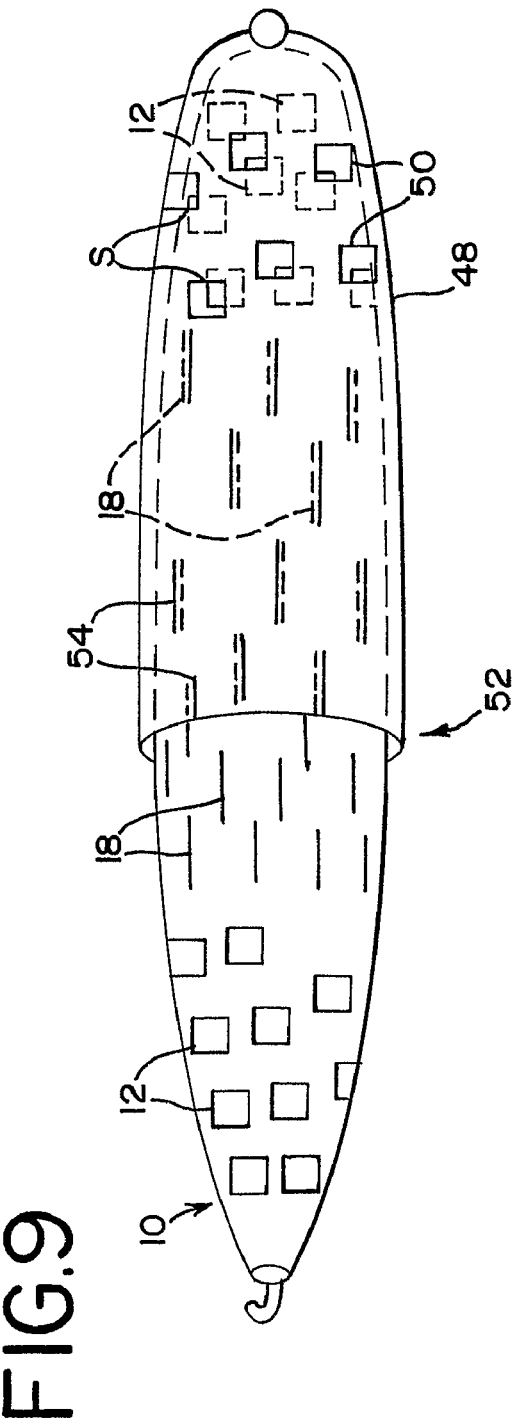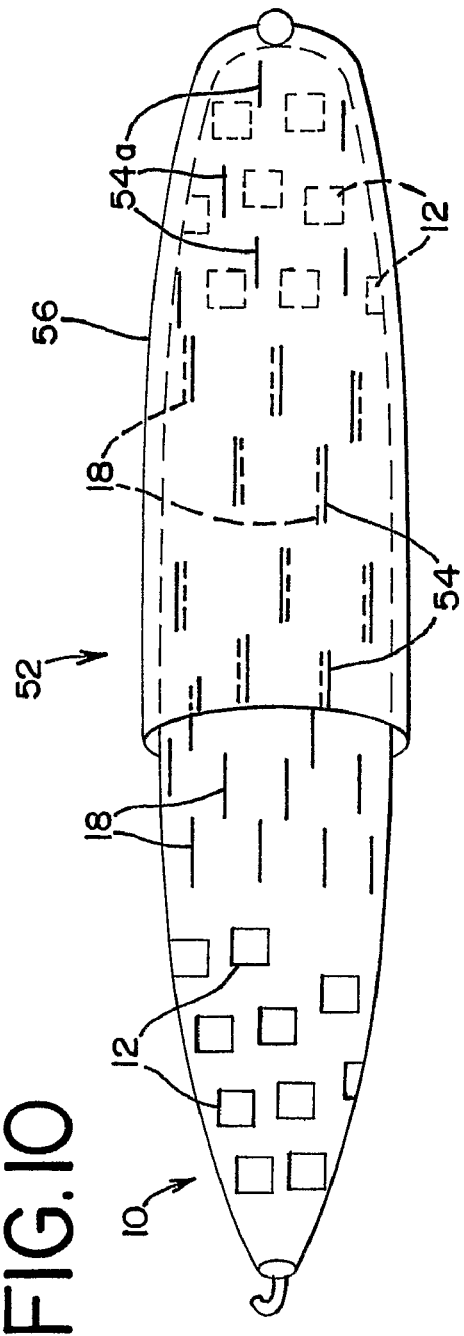

THIN FILM DEVICES FOR TEMPORARY OR PERMANENT OCCLUSION OF A VESSEL

CROSS REFERENCE TO RELATED APPLICATION

This application claims priority from provisional patent application Ser. No. 60/610,777, filed Sep. 17, 2004, which is hereby incorporated herein by reference.

FIELD OF THE INVENTION

This invention generally relates to medical devices that are implantable within a human subject and that have occlusion capabilities that are especially suitable for use as medical device plugs for defective or diseased body vessels. These types of devices have pores which, upon deployment, reverse configuration from open to closed or vice versa for enhanced occlusion, fixation, or other therapeutic capabilities.

DESCRIPTION OF RELATED ART

Medical devices that can benefit from the present invention include those that are characterized by hollow interiors and that are introduced endoluminally and expand when deployed so as to plug up a location of concern within the patient. These are devices that move between collapsed and expanded conditions or configurations for ease of deployment through catheters and introducers. The present disclosure focuses upon occlusion devices for diseased locations within vessels of the body, especially devices sized and configured for implantation within the vasculature, as well as devices for neurovascular use.

A number of technologies are known for fabricating implantable medical devices. Included among these technologies is the use of thin films. Current methods of fabricating thin films (on the order of several microns thick) employ material deposition techniques. These methods are known to make films into basic shapes, such as by depositing onto a mandrel or core so as to make thin films having the shape of the mandrel or core, such as geometric core shapes until the desired amount has built up. Traditionally, a thin film is generated in a simple (oftentimes cylindrical, conical, or hemispherical) form and heat-shaped to create the desired geometry. One example of a known thin film vapor deposition process can be found in Banas and Palmaz U.S. Patent Application Publication No. 2005/0033418, which is hereby incorporated herein by reference.

Methods for manufacturing three-dimensional medical devices using planar films have been suggested, as in U.S. Pat. No. 6,746,890 (Gupta et al.), which is hereby incorporated herein by reference. The method described in Gupta et al. requires multiple layers of film material interspersed with sacrificial material. Accordingly, the methods described therein are time-consuming and complicated because of the need to alternate between film and sacrificial layers.

For some implantable medical devices, it is preferable to use a porous structure. Typically, the pores are added by masking or etching techniques or laser or water jet cutting. When occlusion devices are porous, especially for intercranial use, the pores are extremely small and these types of methods are not always satisfactory and can generate accuracy issues. Approaches such as those proposed by U.S. Patent Application Publication No. 2003/0018381, which is hereby incorporated herein by reference, include vacuum deposition of metals onto a deposition substrate which can include complex geometrical configurations. Microperforations are mentioned for providing geometric distendability and endothelialization. Such microperforations are said to be made by masking and etching or by laser-cutting.

An example of porosity in implantable grafts is Boyle, Marton and Banas U.S. Patent Application Publication No. 2004/0098094, which is hereby incorporated by reference hereinto. This publication proposes endoluminal grafts having a pattern of openings, and indicates that different orientations thereof could be practiced. Underlying stents support a microporous metallic thin film. Also, Schnepp-Pesch and Lindenberg U.S. Pat. No. 5,540,713, which is hereby incorporated by reference hereinto, describes an apparatus for widening a stenosis in a body cavity by using a stent-type of device having slots which open into diamonds when the device is radially expanded.

A problem to be addressed is to provide an occlusion device with portions having reversible porosities that can be delivered endoluminally in surgical applications, while implanting and locating same at the proper site of an occlusion, wherein the porosities reverse in order to provide an at least generally closed portion with an immediate occlusive function to "plug" the vessel defect and control or stop blood flow into the diseased site and an at least generally open portion with filtration or tissue integration properties.

Accordingly, a general aspect or object of the present invention is to provide an occlusion device having portions with varying porosity properties which separately perform a plugging function and a filtration or fixation function upon deployment at or near a diseased site.

Another aspect or object of this invention is to provide a method for plugging a vessel defect that can be performed in a single endoluminal procedure and that positions an occlusion device for effective blood flow control into and around the area of the diseased location.

Another aspect or object of this invention is to provide an improved occlusion device that incorporates thin film metal deposition technology in preparing occlusion devices which exhibit regions of opposing porosity during deployment, which porosity is substantially reversed when properly positioned for occlusion.

Other aspects, objects and advantages of the present invention, including the various features used in various combinations, will be understood from the following description according to preferred embodiments of the present invention, taken in conjunction with the drawings in which certain specific features are shown.

SUMMARY OF THE INVENTION

In accordance with the present invention, an occlusion device is provided that has a thin film structure that has a contracted or collapsed configuration which facilitates endoluminal deployment as well as an expanded or deployed configuration within the body. When in at least the deployed configuration, the thin film is shaped with a converging end of reduced cross-sectional extent when compared with the rest of the deployed device.

Porosity is provided in at least a first portion of the occlusion device in the radially contracted configuration in the form of pores that are generally open when the device is stretched longitudinally. These pores close substantially or fully upon deployment, when the thin film device longitudinally foreshortens and expands radially to shrink the pores to a smaller profile. This slot closure upon expansion provides a porosity that is low enough to fully or partially occlude blood flow to a vessel being treated.

In contrast to these pores, an area having opposing porosity is provided in at least a second portion of the occlusion device. When the term "opposing porosity" is used herein, this refers to an area having pores that are generally closed when the device is in a collapsed configuration for delivery. These pores open upon implantation when the device is deployed to a target occlusion site and expanded. Depending on their location and profile when open, these pores can provide for passage of blood flow to perforator vessels while occluding a diseased location, for body fluid filtration, and/or for tissue fixation (i.e. endothelialization) at or adjacent to the occlusion site. Hence, it will be understood that these two pore areas can be considered to essentially reverse porosities upon deployment, moving from open to closed and vice versa when implanted within the body.

In making the thin film mesh, a core or mandrel is provided which is suited for creating a thin film by a physical vapor deposition technique, such as sputtering. A film material is deposited onto the core or mandrel to form a seamless or continuous three-dimensional layer. The thickness of the film will depend on the particular film material selected, conditions of deposition and so forth. Typically, the core then is removed by chemically dissolving the core, or by other known methods. Manufacturing variations allow the forming of multiple layers of thin film mesh material or a thicker layer of deposited material if desired.

Special application for the present invention has been found for creating porous occlusion devices which have a thin film structure and automatic porosity reversal upon deployment as occlusion devices, and methods also are noted. However, it will be seen that the products and methods described herein are not limited to particular medical devices or methods of manufacture or particular surgical applications.

BRIEF DESCRIPTION OF THE DRAWINGS

FIG. 9 is a front elevational view of an occlusion device in a collapsed configuration according to an alternate embodiment, with portions broken away for clarity; and FIG. 10 is a front elevational view of the occlusion device of FIG. 9 according to an alternate embodiment, with portions broken away for clarity.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 1:
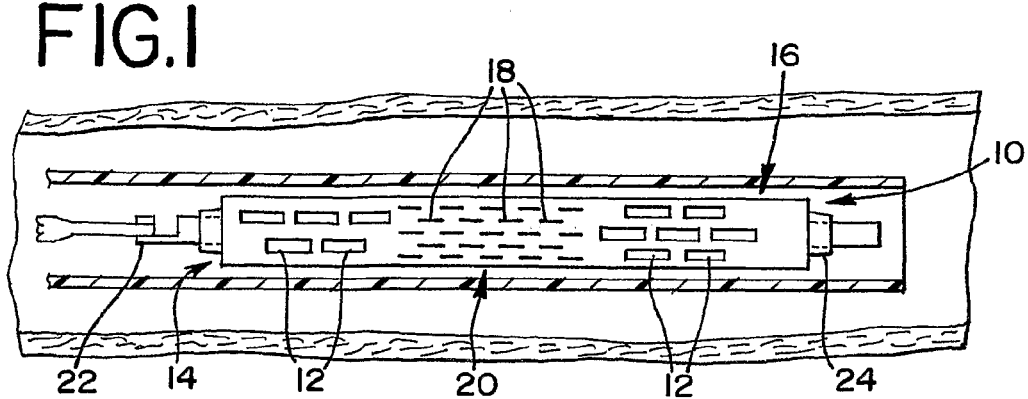
FIG. 1 is a front elevational view of an occlusion device according to the present invention, in a collapsed configuration.

FIG. 1 illustrates an occlusion device 10 in a collapsed position. The occlusion device 10 preferably comprises a thin film mesh formed by physical vapor deposition onto a core or mandrel, as is well-known to those skilled in the art. Most preferably, a thin film of nitinol, or other material which preferably has the ability to take on a shape that had been imparted to it during manufacture, is formed. When nitinol material is used in forming the thin film, the thin film can be at the martensite state. In addition, the thin film when made of nitinol or materials having similar shape memory properties may be austenite with a transition from martensite to austenite, typically when the device is raised to approximately human body temperature, or in the range of about 95 F. to 100 F.

In making the thin film mesh, this selected material is sputter-deposited onto a core, which core is then removed by chemical etching or the like. Examples of this type of deposition are found in US Published Patent Application No. 2003/0018381, No. 2004/0098094 and No. 2005/0033418, incorporated herein by reference. Nitinol, which encompasses alloys of nickel and titanium, is a preferred film material because of its superelastic and shape memory properties, but other known biocompatible compositions with similar characteristics may also be used.

The thickness of the thin film mesh depends on the film material selected, the intended use of the device, the support structure, and other factors. A thin film of nitinol is preferably between about 0.1 and 250 microns thick and typically between about 1 and 30 microns thick. More preferably, the thickness of the thin film mesh is between about 1 and 10 microns or at least about 0.1 micron but less than about 5 microns. A supported mesh may be thinner than a self-supported mesh.

The occlusion device 10 is shown in FIG. 1 in a collapsed configuration in which a plurality of pores or slots 12 disposed along end portions 14 and 16 are substantially open, while a set of generally longitudinal slits 18 located along a body portion 20 between the end portions 14 and 16 are substantially closed. The slots 12 and slits 18 may be formed by any known means, but are preferably formed using laser-cutting. The illustrated slots 12 are shown in FIG. 1 with generally identical rectangular openings which are arranged in a uniform pattern along the end portions 14 and 16, but they may assume other open profiles, e.g. diamond-shaped openings, and be arranged randomly or in selected non-uniform patterns, depending on the intended use. The slits 18 may also assume differing profiles, e.g. curvilinear, and be arranged randomly or in selected non-uniform patterns, according to the intended use. The occlusion device 10 preferably includes a proximal end 14 having a shape that is generally closed, which can culminate in a plasma weld and include an engagement member or hook 22, and a distal end 16 of a shape that is generally closed and that is atraumatically sealed shut by a plasma weld 24 or other suitable seal.

Figure 2:
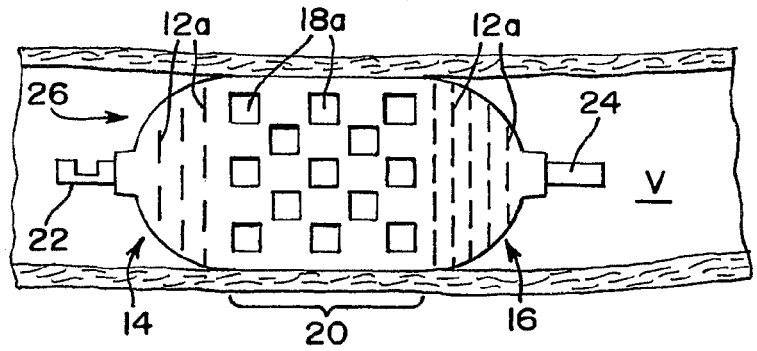
FIG. 2 is a front elevational view of the occlusion device of FIG. 1 in a deployed configuration.

In use, the slots 12 and slits 18 assist in allowing the associated portions of the occlusion device 10 to expand radially. For example, FIG. 2 shows the occlusion device of FIG. 1 when same assumes a longitudinally foreshortened and radially expanded deployed configuration 26 within a body vessel V. When implanted in the body, the occlusion device 10 moves from the elongated, collapsed configuration of FIG. 1 to the foreshortened, deployed configuration 26 of FIG. 2, while the slots move from the open configuration 12 of FIG. 1 to the generally closed configuration 12a of FIG. 2. Compared to the open configuration 12, the slots in the generally closed configuration 12a resemble the closed slits 18 of FIG. 1, but are disposed transversely or generally circumferentially along the end portions 14 and 16. In this closed configuration 12a, the slots provide a decreased porosity and are intended to prevent the flow of blood and other bodily fluids through the associated portion of the occlusion device. Thrombus development occurs and/or occlusion results as generally appreciated in the art.

In contrast to the slots 12, the slits 18 move from the generally closed configuration of FIG. 1 to the generally open configuration 18a of FIG. 2 when the occlusion device has been deployed to the target area. While the slots 12 telescope to cause longitudinal foreshortening and radial expansion, the slits 18 are compressed by the force of the occlusion device moving to its deployed configuration, causing them to narrow and open, thereby contributing to having the associated body portion 20 foreshorten and radially expand. In the open configuration 18a, the slits generally resemble the open slots 12 of FIG. 1, but they may assume other open profiles, such as diamond-shaped openings, depending on their initial closed profile. The open slits 18a abut the walls of the body vessel V and can allow for tissue ingrowth and endothelialization for permanent fixation of the occlusion device.

The configuration of the device 26 as deployed in FIG. 2 is typically achieved by heating a nitinol thin film mesh or other shape memory material when on a shaping core or mandrel until it reaches an austenite condition, whereby it is heat-set into the desired shape. This set shape can be offset when cooled and removed from the mandrel and stretched down to a configuration such as shown in FIG. 1.

Typically, such memory "setting" is adequate to achieve the desired expanded shape of the device. It can be possible to assist this expanded shaping by varying slot or slit size, shape, and location. For example, the elasticity of the mesh can be supplemented in the end portions 14 and 16 adjacent to the body portion 20 by overlaying those portions with relatively large slots that telescope to allow for enhanced radial expansion when the occlusion device moves from a collapsed configuration to a deployed configuration. In contrast, less radial expansion is desired adjacent to the hook 22 and plasma weld 24, so smaller slots that telescope to a lesser extent may be used. Alternatively, if even less radial expansion is required, selected regions may be devoid of slits and slots, which means that the amount of expansion which results is due to the characteristics of the thin film material unaided by slots or slits in the material.

Figure 5:
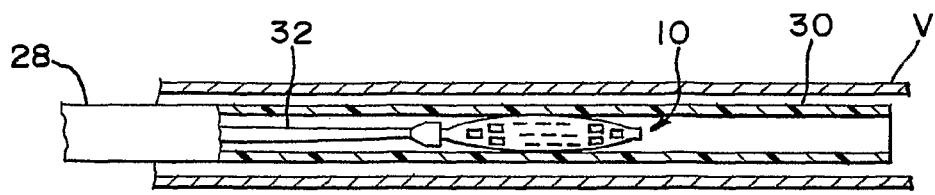
FIG. 5 is a cross-sectional view of the occlusion device of FIG. 1 in a collapsed configuration within a catheter or introducer.

The occlusion device is configured and sized for transport within a catheter or introducer 28 in a collapsed configuration 10, as illustrated in FIGS. 1 and 5. In general, the occlusion device 10 is placed at a downstream end 30 of a catheter 28, which catheter 28 is introduced to the interior of a blood vessel V. The downstream end 30 is positioned adjacent to a region of the blood vessel V which is to be occluded, and then a plunger or pusher member 32 ejects the occlusion device 10 into the target region. This may be achieved by moving the pusher member 32 distally, moving the catheter 28 in a retrograde direction, or a combination of both types of movement.

Figure 6:
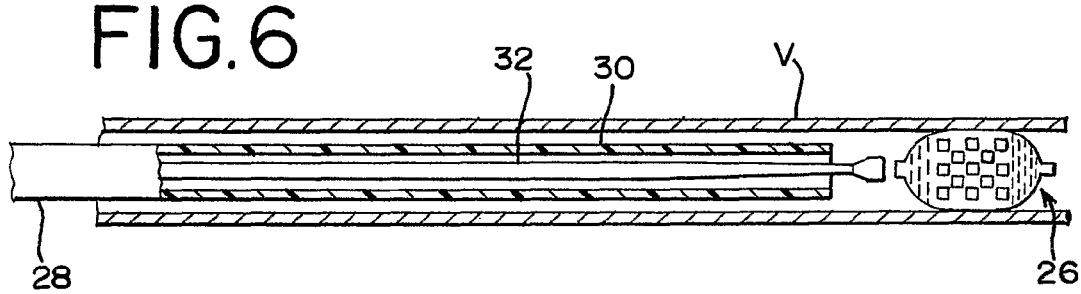
FIG. 6 is a cross-sectional view of the occlusion device of FIG. 5 in a deployed configuration within a body vessel prior to removal of the catheter.

Preferably, the occlusion device 10 is comprised of a shape memory material, such as nitinol, which will move to a deployed configuration 26 upon exposure to living body temperatures, as shown in FIG. 6. When the occlusion device has been placed, the catheter 28 and plunger 32 are thereafter removed from the vessel V, and the occlusion device is left at its deployed location, as shown in FIG. 2.

Figure 3:
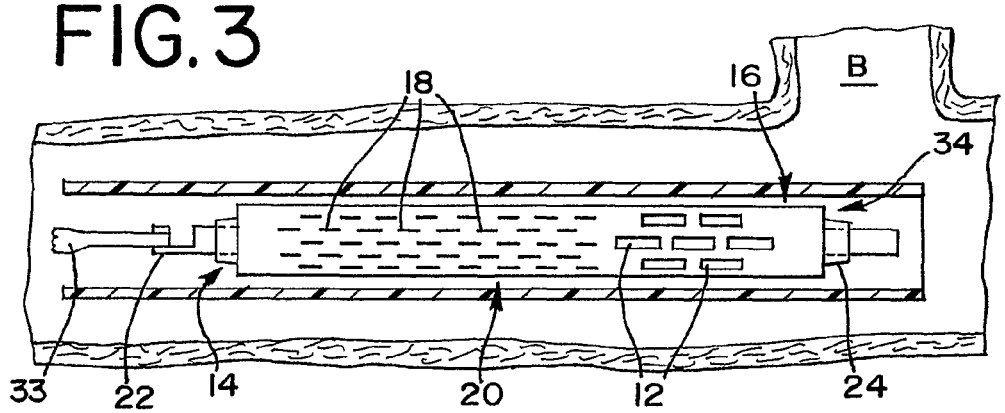
FIG. 3 is a front elevational view of an occlusion device according to an alternate embodiment, in a collapsed configuration adjacent to a branched body vessel.
Figure 4:
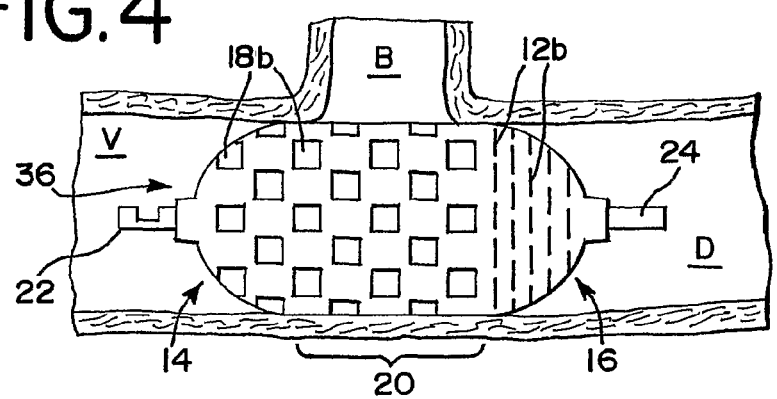
FIG. 4 is a front elevational view of the occlusion device of FIG. 3, in a deployed configuration at a body vessel branch.

FIGS. 5 and 6 illustrate deployment of the occlusion device 10 to a blood vessel V, but the described method can be applied to other body locations, such as to a location in a vessel V that is in the vicinity of a branch B and a diseased area D, as shown in FIGS. 3 and 4. However, for such a treatment site, an alternate occlusion device geometry is preferable. In particular, FIGS. 3 and 4 illustrate an occlusion device 34 suitable for implantation adjacent to a branch B of a body vessel V.

The "branch"-type occlusion device 34 of FIG. 3 is a variation of the occlusion device 10 of FIG. 1. The principal difference is that the proximal end portion 14 of the device 34 of FIG. 3 includes a plurality of generally open slots 12 instead of generally closed slits 18. In all other respects, the "branch"-type occlusion device 34 can be structurally similar to the occlusion device 10 of FIG. 1.

In use, the "branch"-type occlusion device 34 is delivered to the vessel V in an elongated, collapsed configuration, where it is released from a catheter or introducer and allowed to move to a foreshortened, deployed configuration 36, as in FIG. 4. In the illustrated deployed configuration 36, the slots 12 close, as described previously, which causes the distal end portion 16 to radially expand to engage the walls of the vessel V. The deployed configuration with generally closed slots 12b has a decreased porosity and prevents the flow of blood into the diseased area D, which fosters thrombosis and occlusion.

In moving to the deployed configuration 36, the slits 18 of the proximal end portion 14 and body portion 20 move to a generally open configuration 18b, as described previously, which causes the end portion 14 and body portion 20 to radially expand to engage the walls of the vessel V. The open slits 18b define a generally open flow path, which allows blood to flow between the vessel V and the branch B. The slits 18b abutting the walls of the vessel V allow for endothelialization and fixation of the device 36 within the vessel V. Depending on the open profile of the slits 18b, they may also provide a filtering function to prevent the flow of undesirable material between the vessel V and the branch B. They also allow for blood flow to perforator vessels in the vicinity of where the open slits 18b engage the vessel wall.

As described previously with regard to the occlusion device 10 of FIG. 1, the slots 12 and slits 18 of the "branch"-type occlusion device 34 may be of different sizes, configuration, and locations. Although in typical application this variation is not required, it may facilitate the desired expanded shaping, depending on the desired amount of radial expansion and longitudinal foreshortening required at any particular location of the device.

If the occlusion device includes a hook 22, as illustrated in FIGS. 1-4, the device can be removed from the body or readjusted within the vessel V after deployment. The distal end 16 of the occlusion device is inserted into the target region prior to full removal of the proximal end 14 from the distal catheter end 30 in order to minimize the risk of damage to the vessel V and to facilitate removal or location adjustment if needed. To remove or adjust the location of the occlusion device, the process of FIGS. 5 and 6 is essentially reversed, by replacing the pusher member 32 with a pulling member 33 of known construction to engage the hook 22 or the like and to pull the occlusion device into the catheter 28 and engage its walls to reduce its size. When the occlusion device is back in the catheter 28, the catheter 28 is then removed from the vessel V or used to reposition the occlusion device.

Figure 7:
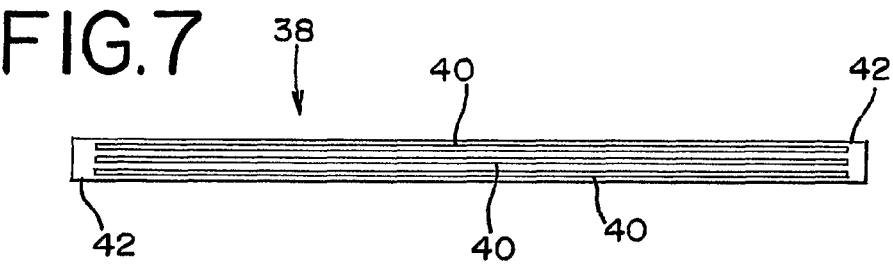
FIG. 7 is a front elevational view of a tube used to form support struts of an alternate embodiment.
Figure 8:
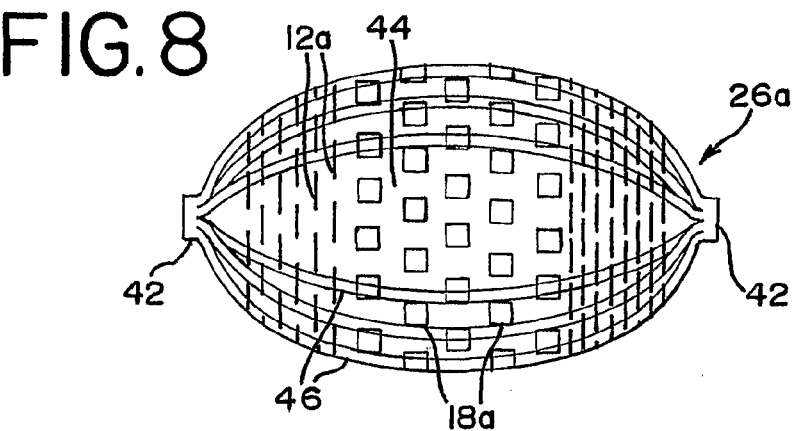
FIG. 8 is a front elevational view of the occlusion device of FIG. 1, with a support structure according to an alternate embodiment.

According to an alternate embodiment of the present invention, the described occlusion devices may be provided with a support structure, similar to that described in U.S. Pat. No. 6,428,558 (Jones and Mitelberg), which is hereby incorporated herein by reference. FIG. 7 shows a generally hollow tube 38 which may be used to make an internal support structure for an occlusion device as illustrated in FIG. 8, or for other devices such as the occlusion device of FIG. 4. The tube 38 is preferably comprised of nitinol or another shape memory material having a wall between about 70 and 250 microns thick, most preferably between about 175 and 225 microns thick. The tube 38 also has at least one region with a plurality of longitudinal cuts 40 and two uncut end portions 42.

In assembling the tube 38, a compressive force is applied to the end portions 42 of the tube 38 until the cuts 40 buckle outwardly to define the struts 46 of FIG. 8. A thin film mesh 44, as illustrated in FIG. 8, may thereafter be laid over the struts 46 and sealed at least along the end portions 42. Alternatively, the tube 38 may be returned to the configuration of FIG. 7 and inserted into the thin film mesh 44 before the sealing step. In another embodiment, the thin film mesh 44 can be positioned inside the tube 38 to provide a device having an external support structure. As a further option, the tube can be positioned between thin film mesh layers to provide an occlusion device having an encapsulated support structure.

The mesh 44 is preferably a biocompatible, flexible material and may be thinner than the thin film of FIGS. 1-4, because it is not required to support itself. The mesh 44 does include a pore structure similar to the self-supporting embodiments, whereby the slots move to a generally closed configuration and the slits move to a generally open configuration when the occlusion device 26a is deployed, as illustrated in FIG. 8. It will be appreciated that, while this aspect of the present invention is shown and described with reference to the occlusion device of FIG. 2, the shape and configuration of the cuts along the tube can be varied so that it can be applied to other occlusion devices according to the present invention. For example, if the cuts 40 are interrupted by an uncut section, a waist will form at the uncut section. In other words, the absence of the cut aspect at a given area will minimize radial expansion thereat while the cut lengths will radially expand upon axial compression.

According to another alternative embodiment of the present invention, the described occlusion devices may be created with an additional outer thin film layer 48, as illustrated in FIG. 9. An occlusion device 10 according to FIG. 1 is nested within a porous thin film layer 48, which is partially broken away in FIG. 9. These layers 10 and 48 operate according to the principles described above. Preferably the two layers 10 and 48 have differing slot patterns or at least slot patterns that are out of phase with each other, such that the slots 12 of the inner layer 10 are misaligned with the slots 50 of the outer layer 48, thereby decreasing the effective slot size S of the layered occlusion device 52. As a result, the layered occlusion device 52 will have substantially the same radially expansive properties according to the present invention, while providing an even lower porosity along the end portions in the deployed configuration, which improves the occlusive properties. This embodiment is useful when cutting technology does not provide slot sizing as small as may be desired in some circumstances.

Unless the slits 18 of the inner layer 10 are substantially aligned with the slits 54 of the outer layer 48, the effective open slit size along the body portion will be diminished in the deployed configuration. Typically, this diminishment will not be complete and blood flow therethrough, even though diminished, can supply perforator vessels with blood flow, oxygen, and the like to maintain these vessels in a healthy condition.

In another embodiment of the device, substantially the same effect of FIG. 9 may be achieved using an outer layer having only longitudinal slits, as illustrated in FIG. 10. Some slits 54 of the outer layer 56 can be aligned with those slits 18 of the inner layer 10 which are to be open in a deployed configuration, while other slits 54a of the outer layer 56 are generally out of phase or misaligned with the slots 12 of the inner layer 10, which are to be closed in a deployed configuration. Accordingly, in a deployed configuration, the aligned slits 18 and 54 of the respective two layers 10 and 56 will define openings, while the misaligned slits 54a and slots 12 will be generally closed. It will be seen that the inner layer may also be provided with only longitudinal slits, and substantially the same pattern of alignment and misalignment may be practiced in order to define open and closed portions of the deployed device. The exclusive use of slits may be preferred in some instances where it is difficult to provide adequate slots for the collapsed configuration.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A thin film occlusion device for occluding at least a portion of a body vessel in a human subject, comprising a thin film mesh including:
   a distal end portion having a substantially closed end configuration;
   a proximal end portion;
   a body portion extending between said distal end portion and said proximal end portion;
   a plurality of slot members associated with at least a selected one of said body portion, distal end portion, and proximal end portion; and
   a plurality of slit members associated with at least a selected one of said body portion, distal end portion, and proximal end portion, wherein said slot members and said slit members are positioned at different locations along the occlusion device;
   said slot members are in a generally open condition and said slit members are in a generally closed condition when the occlusion device is in a collapsed orientation suitable for passage through a medical delivery apparatus; and
   said slot members are in a generally closed condition and said slit members are in a generally open condition with radial expansion movement of the occlusion device to a deployed orientation for occlusion action within a body vessel.

2. The thin film occlusion device of claim 1, further comprising an engagement member associated with said proximal end portion for selective removal of the occlusion device from a body vessel or repositioning of the occlusion device in a body vessel.

3. The thin film occlusion device of claim 1, further comprising a support structure of the occlusion device for supporting at least one of said distal end portion, proximal end portion, and body portion.

4. The thin film occlusion device of claim 1, further comprising a plurality of thin film layers, each having a plurality of slit members.

5. The thin film occlusion device of claim 1, wherein at least the portions associated with said slot members and said slit members longitudinally foreshorten and radially expand upon movement of the occlusion device to the deployed configuration.

6. The thin film occlusion device of claim 1, wherein said body portion, distal end portion, and proximal end portion are comprised of a material having shape memory properties.

7. The thin film occlusion device of claim 6, wherein said material having shape memory properties is nitinol.

8. The thin film occlusion device of claim 7, wherein said nitinol is a martensite thin film.

9. The thin film occlusion device of claim 7, wherein said nitinol is an austenite thin film that transitions from martensite to austenite upon exposure to human body temperature.

10. The thin film occlusion device of claim 1, wherein said body portion, distal end portion, and proximal end portion are comprised of a material having a thickness greater than about 0.1 microns and less than about 5 microns.

11. A thin film occlusion device for occluding at least a portion of a body vessel in a human subject, comprising a thin film mesh including:
   a distal end portion having a substantially closed end configuration;
   a proximal end portion having a substantially closed end configuration;
   a body portion extending between said distal end portion and said proximal end portion;
   a plurality of slots associated with said distal end portion and said proximal end portion, wherein said slots are capable of movement from a generally open condition to a generally closed condition and wherein the movement causes at least said distal end portion and said proximal end portion to longitudinally foreshorten and radially expand; and
   a plurality of slits associated with said body portion, wherein said slits are capable of movement from a generally closed condition to a generally open condition and wherein the movement causes at least said body portion to longitudinally foreshorten and radially expand.

12. The thin film occlusion device of claim 11, further comprising a support structure of the occlusion device for supporting at least one of said distal end portion, proximal end portion, and body portion.

13. The thin film occlusion device of claim 11, further comprising a plurality of thin film layers, each having a plurality of slits, and at least some of said slits of one of said film layers are out of alignment with any slit of another of said film layers.

14. The thin film occlusion device of claim 11, wherein said body portion, distal end portion, and proximal end portion are comprised of a material having shape memory properties.

15. The thin film occlusion device of claim 14, wherein said material having shape memory properties is nitinol.

16. A thin film occlusion device for occluding at least a portion of a body vessel in a human subject, comprising a thin film mesh including:
   a distal end portion having a substantially closed end configuration;
   a proximal end portion having a substantially closed end configuration;
   a body portion extending between said distal end portion and said proximal end portion;
   a plurality of slots associated with said distal end portion, wherein said slots are capable of movement from a generally open condition to a generally closed condition and wherein the movement causes at least said distal end portion to longitudinally foreshorten and radially expand; and
   a plurality of slits associated with said proximal end portion and said body portion, wherein said slits are capable of movement from a generally closed condition to a generally open condition and wherein the movement causes at least said proximal end portion and said body portion to longitudinally foreshorten and radially expand.

17. The thin film occlusion device of claim 16, further comprising a support structure of the occlusion device for supporting at least one of said distal end portion, proximal end portion, and body portion.

18. The thin film occlusion device of claim 16, further comprising a plurality of thin film layers, each having a plurality of slits, and at least some of said slits of one of said film layers are not in full alignment with any slit of another of said film layers.

19. The thin film occlusion device of claim 18, wherein each of said film layers includes a plurality of slots.

20. The thin film occlusion device of claim 16, wherein said body portion, distal end portion, and proximal end portion are comprised of a material having shape memory properties.

21. The thin film occlusion device of claim 20, wherein said material having shape memory properties is nitinol.

* * * * *